(12) United States Patent
Wortelboer (10) Patent No.: US 11,076,751 B2
(45) Date of Patent: Aug. 3, 2021

(54) IMAGING SYSTEM, OPTICAL ELEMENT, AND A CATHETER OR ENDOSCOPE USING THE SAME

(71) Applicant: KONINKLIJKE PHILIPS N.V., Eindhoven (NL)

(72) Inventor: Pippinus Maarten Robertus Wortelboer, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 485 days.

(21) Appl. No.: 15/736,091

(22) PCT Filed: Jun. 13, 2016

(86) PCT No.: PCT/EP2016/063417
§ 371 (c)(1),
(2) Date: Dec. 13, 2017

(87) PCT Pub. No.: WO2016/202710
PCT Pub. Date: Dec. 22, 2016

(65) Prior Publication Data
US 2018/0177386 A1 Jun. 28, 2018

(30) Foreign Application Priority Data
Jun. 19, 2015 (EP) .................................... 15172925

(51) Int. Cl.
*A61B 1/06* (2006.01)
*A61B 1/00* (2006.01)
(Continued)

(52) U.S. Cl.
CPC ........ *A61B 1/0615* (2013.01); *A61B 1/00177* (2013.01); *A61B 1/00181* (2013.01);
(Continued)

(58) Field of Classification Search
CPC ............ G02B 17/0872; G02B 23/2446; G02B 23/2461; A61B 1/0615; A61B 1/00177;
(Continued)

(56) References Cited

U.S. PATENT DOCUMENTS

| | | | | |
|---|---|---|---|---|
| 5,235,470 A | * | 8/1993 | Cheng | ........................ F21V 7/09 359/852 |
| 5,272,408 A | * | 12/1993 | Levin | ........................ F21V 7/09 313/113 |

(Continued)

FOREIGN PATENT DOCUMENTS

| | | |
|---|---|---|
| JP | 1171353 A | 7/1989 |
| JP | 2008268240 A | 11/2008 |

(Continued)

*Primary Examiner* — Timothy J Neal
*Assistant Examiner* — Jae Woo (57) ABSTRACT

The invention provides an imaging system comprising an optical element for deflecting axially incident light into a series of axially spaced outward radial projections, and further comprising an image collection means for collecting reflected light. The element comprises a plurality of light deflecting surfaces or features which are arranged at axially successive points along the element, each at a different radial location. The light-deflecting surfaces are arranged to deflect light incident upon them from an axial direction in a radial direction, each thereby generating a radial projection of light from the element. A beam or beam bundle projected along the element has successive outer annular layers stripped by the facets and deflected outwards at different axial points along the structure.

18 Claims, 6 Drawing Sheets

(51) Int. Cl.
  *G02B 23/24* (2006.01)
  *G02B 17/08* (2006.01)
  *G02B 27/14* (2006.01)
  *G03B 15/05* (2021.01)
  *G03B 37/00* (2021.01)
  *A61B 1/07* (2006.01)
  *A61B 1/267* (2006.01)
  *A61B 5/00* (2006.01)
  *H04N 5/225* (2006.01)

(52) U.S. Cl.
  CPC .......... *A61B 1/0607* (2013.01); *A61B 1/0661* (2013.01); *A61B 1/07* (2013.01); *A61B 1/267* (2013.01); *A61B 5/0084* (2013.01); *G02B 17/0872* (2013.01); *G02B 23/2446* (2013.01); *G02B 23/2461* (2013.01); *G02B 27/143* (2013.01); *G03B 15/05* (2013.01); *G03B 37/005* (2013.01); *H04N 5/2256* (2013.01); *G03B 2215/0582* (2013.01); *H04N 2005/2255* (2013.01)

(58) Field of Classification Search
  CPC . A61B 1/00181; A61B 1/0607; A61B 1/0661; A61B 1/07; A61B 1/276
  See application file for complete search history.

(56) References Cited

U.S. PATENT DOCUMENTS

| | | | | |
|---|---|---|---|---|
| 5,303,026 A | * | 4/1994 | Strobl | G01N 21/645 250/458.1 |
| 5,512,759 A | * | 4/1996 | Sweatt | G03F 7/702 250/492.1 |
| 5,613,769 A | * | 3/1997 | Parkyn, Jr. | G02B 19/009 362/338 |
| 5,655,832 A | * | 8/1997 | Pelka | F24S 23/31 362/296.09 |
| 5,801,889 A | * | 9/1998 | Meyers | G02B 5/1876 359/520 |
| 5,806,955 A | * | 9/1998 | Parkyn, Jr. | F21V 7/0091 362/612 |
| 5,812,252 A | * | 9/1998 | Bowker | F41A 17/066 356/71 |
| 5,897,201 A | * | 4/1999 | Simon | G02B 6/0068 362/268 |
| 6,031,958 A | * | 2/2000 | McGaffigan | B29D 11/00663 362/555 |
| 6,536,921 B1 | * | 3/2003 | Simon | F21S 6/005 362/268 |
| 6,701,181 B2 | * | 3/2004 | Tang | A61B 1/00096 385/115 |
| 7,102,824 B2 | * | 9/2006 | Clark | G02B 3/08 257/436 |
| 7,558,455 B2 | * | 7/2009 | Weir | A61B 1/00096 385/119 |
| 8,386,023 B2 | | 2/2013 | Furnish | |
| 2003/0230715 A1 | | 12/2003 | Remillard et al. | |
| 2004/0109164 A1 | * | 6/2004 | Horii | G01B 9/0201 356/479 |
| 2005/0024744 A1 | * | 2/2005 | Falicoff | G02B 3/04 359/737 |
| 2007/0270717 A1 | | 11/2007 | Tang et al. | |
| 2008/0170284 A1 | * | 7/2008 | Hayashi | B41J 2/471 359/216.1 |
| 2009/0326385 A1 | | 12/2009 | Hendriks et al. | |
| 2011/0001984 A1 | * | 1/2011 | Keller | G02B 13/06 356/612 |
| 2013/0250609 A1 | | 9/2013 | Morgan et al. | |
| 2016/0153765 A1 | | 6/2016 | Yamazaki et al. | |

FOREIGN PATENT DOCUMENTS

| | | |
|---|---|---|
| KR | 2013034573 A | 4/2013 |
| WO | 2004078044 A1 | 9/2004 |
| WO | 2007138552 A2 | 12/2007 |
| WO | 2008019359 A2 | 2/2008 |
| WO | 2015162140 A1 | 10/2015 |

\* cited by examiner

IMAGING SYSTEM, OPTICAL ELEMENT, AND A CATHETER OR ENDOSCOPE USING THE SAME

CROSS-REFERENCE TO PRIOR APPLICATIONS

This application is the U.S. National Phase application under 35 U.S.C. § 371 of International Application Serial No. PCT/EP2016/063417, filed on 13 Jun. 2016, which claims the benefit of European Application No. 15172925.8, filed on 19 Jun. 2015. These applications are hereby incorporated by reference herein.

FIELD OF THE INVENTION

The invention relates to an imaging system comprising an optical element, in particular an element for deflecting axially directed light into a radial direction.

BACKGROUND OF THE INVENTION

For many endoscopic procedures, in particular procedures for inspecting or investigating the patency of the human upper airway, it is desirable that an endoscope has a light generating means capable of producing an outwardly directed ring (or radial plane) of light, such that when inserted into a tube-like airway, cross sectional contours of the airway may be illuminated for inspection by a camera.

One known means of providing such a light pattern is to direct collimated laser light from an optical fibre toward a deflecting cone whose pitch is such as to deflect the incident light at 90 degrees from its surface in all directions around it. The effect is to create a 'ring' pattern of light projecting outwards from the cone, which may then be used to illuminate a circumferential section of an airway. In particular, there are two variations of this concept. In a first, the cone has a reflective outer surface, and is arranged with its tip facing in the direction of the oncoming light, such that light is reflected directly out from its surface. In a second, the cone is arranged with its base facing toward the oncoming light and the pitch arranged such that light incident from the optical fibre on the internal walls of the cone is reflected by total internal reflection in the direction of the opposing wall, though which it is transmitted, deflecting due to refraction as it does so into a path which is at 90 degrees to the initial incident light.

In many instances however, it is desirable to create multiple ring patterns of light, at a series of spaced points along the airway, in order to reliably inspect its patency. Presently, this can only be achieved by means of providing multiple illumination units along the catheter, each with its own laser, optical fibre (optionally a GRIN lens) and cone. This renders the resulting catheter both cumbersome and also expensive to produce.

Desired therefore is an optical device which can facilitate the generation and imaging of multiple, axially spaced, ring patterns of light, utilising just a single source of light.

SUMMARY OF THE INVENTION

The invention is defined by the claims.

According to an aspect of the invention, there is provided an an imaging system for imaging an internal cavity, comprising:

an optical element, comprising
an optical body having axial extension and radial extension, for receiving an input beam-front which propagates in the axial direction, and deflecting said input beam front into a series of axially spaced annular projections of light 40, and
a plurality of beam-deflecting facets (32, 70, 72), axially and radially separated with respect to one another, with non-beam-deflecting spaces in between, wherein the beam-deflecting facets are arranged along the optical body and configured to intercept and deflect different annular portions of the input beam-front outwards from the optical body, in a radial direction, to thereby generate from the optical element a series of axially separated annular projections of light; and
an image collection means for collecting light reflected from one or more surfaces of the internal cavity.

By spacing the beam-deflecting facets radially from one another (as well as axially) each facet may be arranged to receive an annular 'layer' or section of an overall beam or beam bundle being propagated through or along the optical body. In this way the facets may be used effectively as radial 'selectors'; each arranged to, at a different axial position along the element, effectively 'strip out' just one ring, or radial layer, of propagating light and deflect it radially outwards from the element. The effect is to create propagating from the element a series of axially spaced planes of light, each projected radially outward from the element. When incident upon walls of a patient's airway, for example, these may form spaced annuli of light which enable inspection of multiple sections of the airway. At least one image collection means is further provided, to collect and/or capture reflections of the spaced annuli of light from the internal walls of the cavity, thereby providing an integrated imaging system for imaging axially spaced portions of the internal cavity.

In examples, the image collection means may comprise one or more optical elements for collecting and/or redirecting light or images reflected from the walls of the internal cavity. Image collection means in examples may include one or more lenses, mirrors, other reflecting or deflecting elements, or optical fibres. Optical fibres may enable light or images collected from the walls of the cavity to be optically communicated to an external image capturing element, such as a camera for example. According to further examples however, the image collection means may comprise one or more image capturing elements, such as camera elements, for capturing the reflected light and generating image data as an output.

According to examples, multiple image collection means may be provided to facilitate imaging of different axial zones or regions, or a single means may be provided capable of collecting reflections of all of the annular projections. These may include a separate camera element for instance provided at multiple points along the element, or may instead comprise multiple lenses and or optical fibres disposed at a plurality of points along the element, configured to collect reflections of each of the annular projections and to optically transmit or propagate them, via the optical fibres, to an image capturing element such as a camera (either externally provided, or provided as part of the invention).

The optical element comprises a primary optical body or core, having axial extension and radial extension. The element is configured to receive an input beam front at a first axial end or proximal axial region and to facilitate delivery of successive annular portions of said input beam front onto axially spaced beam deflecting facets arranged along the optical body. In at least some examples, the optical body is configured to transmit or transport the input beam through and along the volume of the optical body. In this case, the optical body may in some cases comprise an optical fibre for instance, or alternatively may comprise any optical unit or component configured to transport, or allow passage of, an input beam front along its length, through the bulk of the material of the body itself.

In other examples, however, the optical body may not transmit the beam-front through its volume, but may instead simply form a central optical structure configured to facilitate successive deflection or reflection of axial portions of an input beam front which is propagating through the the air (or other medium) immediately surrounding the optical body. In examples to be described in greater detail below for instance, the optical body comprises a radially tapered optical structure, having radial extension which increases along its axial length, and having beam-deflecting facets arranged at axially successive points along its (expanding) radial periphery. When a beam-front is propagated toward the proximal axial end of the body, along an optical axis substantially coincident with the axial axis of the optical body, the beam-front is essentially pierced by the optical body, and, and it travels along the length of the body, successive inner annular sections of the beam front fall incident at the successively arranged deflecting facets arranged along the outside of the optical body.

In all examples, the optical body consists of a single, cohesive, unitary body, capable of receiving a single beam-front extending across the entire radial extension of the body and deflecting said single beam-front into a series of axially spaced annular projections of light. In this way, the optical body is distinguished for example from alternative optical structures which may comprise for instance an assembly of optical parts housed within a casing or housing. The optical element is formed from at least a combination of the optical body and the beam-deflecting facets, which may be in direct optical communication with the optical body, such that the two optically collaborate to receive, transport and defect an input beam-front into a plurality of output annular projections.

Note that the term 'annular' in this context is not to be understood as limiting to a circular shape. An annulus for the present purposes is to be understood to mean any closed loop or ring about a central opening, the closed loop or ring having any particular shape, including, but not limited to circular, elliptical, square, oblong, triangular or hexagonal. By 'annular' is meant following the shape or form of such an annulus, but not necessarily continuously or completely. An annular projection of light may comprise, for example, a projection which follows the shape of just one section or portion of an annulus.

The annular projections of light, therefore, may in some examples comprise continuous annular projections, but may in other examples comprise non-continuous annular projections. Similarly, the annular portions of the input beam-front deflected by the beam-deflecting elements may in certain examples comprise a continuous or complete annulus of light, but may in other examples comprise just an azimuthal section of a complete annulus.

Although the optical body of the optical element is defined in terms of radial and axial extensions, these are not to be understood as limiting the optical element to a cylindrical or substantially cylindrical shape. The body might in various non-limiting examples comprise a circular, elliptical, square, oblong, triangular or hexagonal cross-section. The radial extension of the body is to be understood simply as meaning the extension of the body in directions perpendicular to the axial direction. Similarly, a 'radial direction' in this context may refer to any direction which is perpendicular to the axial direction/extension of the element or body. The beam-deflecting facets, in examples, may be adapted to deflect axially incident light in any radial direction, i.e. any direction perpendicular to the axial, and not necessarily, for example, in the particular radial direction defined by a vector extending perpendicularly from the central axial axis to the position of the facet. The radial extension of the optical body, at any given axial point, may not be uniform in all radial directions (as would be the case for a cylinder), but may vary to produce any of a range of polygonal shapes.

Note further that by 'axial' is meant aligned with a central longitudinal axis of the optical element or body, said axis defining a radial origin of the element or body along its length. This axial or longitudinal axis need not be linear, but could be curved for example. This may the case where the optical body is formed from a flexible optical fibre for instance.

The beam deflecting facets may comprise any form of surface, façade, face or surface portion adapted to deflect axially incident light in a radial direction. The facets may in some examples comprise surfaces which have been cut (for example from the body or volume of the optical body) such that they redirect light in a desired direction, but may in other examples comprise dedicated optical elements such as mirror elements, reflector elements or microprisms for instance.

The beam-deflecting facets may, in examples, comprise annular facets shaped and arranged extending circumferentially around the entire periphery of the optical body. In other cases, the beam-deflecting facets may be shaped and arranged to extend around just a portion of the periphery of the body, to thereby form annular sections or portions.

Each beam deflecting facet may be so radially separated from its neighbours that their surfaces are radially non-overlapping. In this way each facet is arranged to coincide with a distinct radial portion or layer of the beam or beam bundle. In some examples, the facets may be so radially arranged that their surfaces are radially contiguous with one another. In this way, none of the source light is wasted, since successively deflected radial 'layers' of the input beam or beam bundle are contiguous.

Although the beam deflecting facets may be arranged radially contiguously, the axial arrangement of their surfaces is not contiguous. The object of embodiments of the invention is to generate a longitudinal beam pattern comprising a series of axially separated/spaced projections. Axially contiguous beam-deflecting facets would not achieve this.

Note that by radially-directed is meant at least partially or substantially radially directed. In particular, the essential feature is that the beam deflecting facets deflect (axially) incident light radially, i.e. they act to increase the radial component of the incident rays' propagation direction.

The radial extension of the element or optical body may vary along the axial direction, and the deflecting facets may be arranged at axially successive points along a radial periphery of the optical body.

By radial periphery is meant the exterior surface or boundary of the optical body, extending around its central axial or longitudinal axis.

The radial extension of the element or body may progressively decrease or progressively increase along the axial direction. In this way, the axially successive facets are arranged to respectively deflect radially adjacent layers of the input beam or beam bundle. Such an arrangement is not necessary, but may for example simplify manufacture of the element.

In some examples, the overall envelope of radial extension of the optical body, excluding any protrusions or depressions formed by the beam-deflecting facets may vary continuously along the axial direction. The optical body may for example comprise a primary core structure, extending axially, and having continuously varying radial extension, and wherein the beam deflecting facets are built into or onto said core structure, for example in the form of notches or reflective protrusions. By 'envelope' is meant the shape/structure of the primary core of the element, excluding any smaller features formed by the deflecting facets.

As opposed to varying continuously, the radial extension of the optical body or element may in examples vary stepwise along the axial direction, such that the radial periphery of the element comprises a series of axially spaced stepped portions.

In these cases, the beam-deflecting facets may be comprised by reflecting elements, each having a reflective surface arranged facing one of said stepped portions, and angled so as to reflect axially incident light outward from the element in a radial direction. The stepped portions may in some cases comprise directly radially parallel (i.e. 'vertical') steps, or may comprise slanted or angled steps. Each beam deflecting facet may be arranged, for example, having a reflective surface facing toward each radially parallel or angled step, such that light transmitted through the straight or slanted surface of the step is incident on the facet surface and deflected by it.

In other examples, the beam-deflecting facets may partly delimit the radial periphery of the optical body. In this case, the beam deflecting facets are built into the core structure of the element itself. In the case that the overall radial periphery varies continuously and monotonically, the beam deflecting facets may comprise surfaces of a series of axially spaced notches formed in the optical body or core structure. Alternatively, the stepped sections of the radial periphery themselves may form the deflecting facets.

Each beam-deflecting facet may be arranged to deflect light outwards from the element via a corresponding transmission facet positioned at a radially opposite point on the radial periphery, said point positioned along an optical path through the optical body from the deflection facet.

In this case, light axially incident at a beam deflecting facet is redirected inwards, toward the radial centre of the optical body, and exits the structure at the radially opposite side through a specially provided transmission facet, axially arranged so as to coincide with the deflected beam on reaching the edge of the structure, and having a surface angled so as to transmit and not reflect as much of the light as possible. According to these examples, each transmission facet may be built into the core of the element itself (i.e. partly delimit the radial periphery of the optical body) and the reflection from the deflection facet may be through total internal reflection.

Furthermore, within the above example, for each transmission facet, there may in addition be provided, at a radially parallel and axially adjacent point along the radial periphery, a corresponding blocking facet, arranged to reflect rays incident from an axial direction, to prevent said rays being transmitted through the corresponding transmission facet.

It is important that the transmission facet does not transmit light which is incident from an axial direction, as this would lead to stray light escaping through these facets, interfering with the generated ring patterns. The blocking facets effectively hide the transmission facet from axially directed rays. The blocking facets may be formed of a transparent material, but be specially angled so as to reflect axially incident light, rather than transmit it.

Note that in one set of examples, the blocking facet itself may also perform the role of deflection facet, redirecting light—in similar fashion to the first deflection facet—across the body of the element in the direction of a co-operatively arranged second transmission facet, positioned radially parallel and axially adjacent to the first deflection facet. Within this arrangement, the first deflection facet may furthermore play a secondary role as blocking facet to the second transmission facet.

Within the above-described examples, the radial extension of the optical body of the element may decrease along the axial direction, wherein, for at least an axial portion of the element, the radial extensions $r_i$ at axially successive deflection facets may conform to $$r_{i+1} \geq \frac{\tan\mu - \tan\varphi}{\tan\mu + \tan\varphi} r_i$$

where $\mu$=angle of the deflection facet, and $\varphi$=propagation angle of the beam(s), with respect to a radial direction, after reflection by the deflection facet.

The decline in radial extension facilitates the radial separation between axially successive deflection facets—which are located at the radial periphery of the optical body. The radius declines to allow successive facets to be aligned with a distinct annular layer or portion of the beam or beam bundle propagated axially along the element, without interfering with any other annular portion. The radial change between successive deflection facets may for example be equal to the (resolved) radial 'height' of the preceding deflection fact. Up to a point the radial change between successive deflection facets may be equal. However, after a critical point, the radial change must begin to decrease for successive facets, in order to avoid the axial separation between each blocking facet and its respective transmission facet becoming negative (i.e. there being no separation between them). This begins to occur after the critical point due to the angular constraints of the deflected light path.

According to any example embodiment, the optical element may comprise an optical fibre. The optical fibre may be spatially separated from the optical body or primary optical component comprising the deflection and/or transmission facets. The optical fibre in this case provides a medium through which to propagate the light beams on their journey to the deflecting part of the arrangement. A gradient index (GRIN) lens located after the general light feeding fibre can, in examples, be used to collimate the light that goes into the optical body. Alternatively, the optical body itself may be formed from an optical fibre, wherein the deflecting facets are built into or onto said core fibre.

According to any example embodiment, the image collection means may comprise a camera element. In examples, this may be a single camera element having a field of view capable of capturing all of the annular projections generated by the optical element upon reflection from the internal walls of a cavity being imaged. In examples, a provided camera element may have a plurality of sensitive portions or regions, configured to image or capture light from different axial or radial regions of the cavity being imaged, or to capture different of the annular projections, In further examples, there may be provided a plurality of camera elements for capturing light from a respective plurality of axial or radial regions of the cavity being imaged, or to image or capture light from different of the annular projections, or different radial sections of one or more of the annular projections.

In yet further examples, there may instead be provided a single camera element in combination with a plurality of image collection elements provided at different axial locations, configured to collect light reflected from a respective plurality of axial regions of the internal cavity, and to redirect or optically communicate or transmit it to the single provided camera element. These may include by way of example a plurality of lenses and/or optical fibres.

According to an aspect of the invention, there is provided a catheter or endoscope comprising:
  a beam generating means; and
  an imaging system as claimed in any preceding claim, the optical element of which being in optical communication with said beam generating means and arranged so as to deflect light from the beam generating means radially outward from the catheter or endoscope.

According to a further aspect of the invention, there is additionally provided a method of imaging an internal cavity including deflecting axially propagated light to form a series of axially spaced, annular projections, the method comprising:
  propagating an input beam-front in an axial direction along an optical body comprised by an optical element, the optical element being positioned within the internal cavity, and said optical body having axial extension and radial extension, wherein the optical element further comprises a plurality of beam-deflecting facets, the beam-deflecting facets being axially and radially separated with respect to one another, with non beam-deflecting spaces in between, and arranged so as to intercept and deflect different annular portions of the input beam-front outwards from the optical element, in a radial direction, to thereby generate from the optical element a series of axially separated annular projections of light; and
  collecting light reflected by one or more surfaces of the internal cavity by means of an image collection means, to thereby enable imaging of the internal cavity.

According to various embodiments of this method, the input beam-front may be a laser beam front.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides an optical element for deflecting axially incident light into a series of axially spaced outward radial projections. The element comprises a plurality of light deflecting surfaces or features which are arranged at axially successive points along the element, each at a different radial location. The light-deflecting surfaces are arranged to deflect light incident upon them from an axial direction in a radial direction, each thereby generating a radial projection of light from the element. A beam or beam bundle projected along the element has successive outer annular layers stripped by the facets and deflected outwards at different axial points along the structure.

Figure 1:
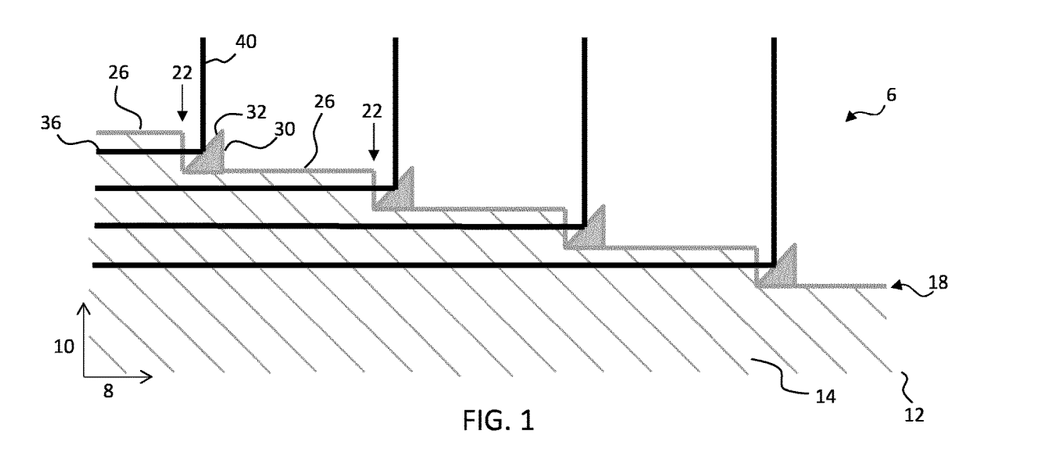
FIG. 1 schematically depicts a first example optical element.

In FIG. 1 is illustrated a cross-section through a first example optical element 6 in accordance with embodiments of the invention. The element 6 has axial 8 and radial 10 extensions, and is axisymmetric about a central axial axis 12. For the purposes of illustration, only a top half of the element is shown in the Figure. The element 6 comprises a primary optical body consisting of a transparent optical fibre 14 having a stepwise decreasing radius. The radial periphery 18 of the optical fibre comprises a series of axially spaced 'vertical' step portions 22, separated by a correspondingly spaced series of axially (or azimuthally) 'flat' portions 26. Since the element is axisymmetric, the flat portions 26 effectively define a series of adjoined cylinders of ever decreasing radius. Adjacent to each step portion 22, a circular or ringed optical structure 30 is positioned, extending circumferentially around the optical fibre, and having an inclined surface 32 facing in the direction of the step portion at an angle of around 45 degrees with respect to it.

As illustrated in the figure, when collimated light 36 is directed axially (horizontally) along the length of the element 6, light rays or beams which are propagating at different radial levels within the element are intercepted at different axial points by the successively arranged optical ring structures 30 of progressively decreasing radii. The reflective inclined surfaces (or facets) 32 act to deflect the light 36 incident upon them from the axial direction and redirect it in a radial direction, to form a series of axially spaced circular (or ringed) projections of light 40. The width of the generated ring is dependent upon the width of the beam incident at the deflecting facet 32, with a maximum width constrained by the surface area of the facet 32 itself.

Note that in the figure, the source light 36 is schematically depicted by means of a plurality of discrete, radially separated rays, each shown propagating along a path which coincides with one of the beam deflecting facets 32. This is purely for purposes of illustration however, and in reality the source light may typically comprise an input beam, having a beam front which extends continuously across the radial plane of the element. In some cases, the source light may comprise an input beam bundle, formed of a plurality of radially contiguous beams, arranged to propagate in parallel along the axial extension of the element. In either case, each beam-deflecting facet 32 is arranged so as to intercept a distinct annular section or layer of the input beam or beam bundle, and not merely an individual ray or beam.

The source of collimated light may be delivered for example by a (separately provided) laser, in combination with an optical collimating element, such as for example a gradient index (GRIN) lens. Other collimating elements might also be used however, such as TIR collimators, collimating channels, Fresnel lenses or Fresnel foils.

Although in the particular example of FIG. 1, the optical element 6 is substantially cylindrical in shape, in alternative examples, the element may have a different 3D structure. For example, the element might be a cuboid of successively decreasing height. In this case, there may be generated a linear 'plane' of light at each of the four sides of the element. The element would in this case hence produce a series of discontinuous (rectangular) annular projections of light, axially spaced along the length of the element. Other regular 'prisms' of differently numbered sides might also be considered, in order to generate other projection patterns.

Figure 2:
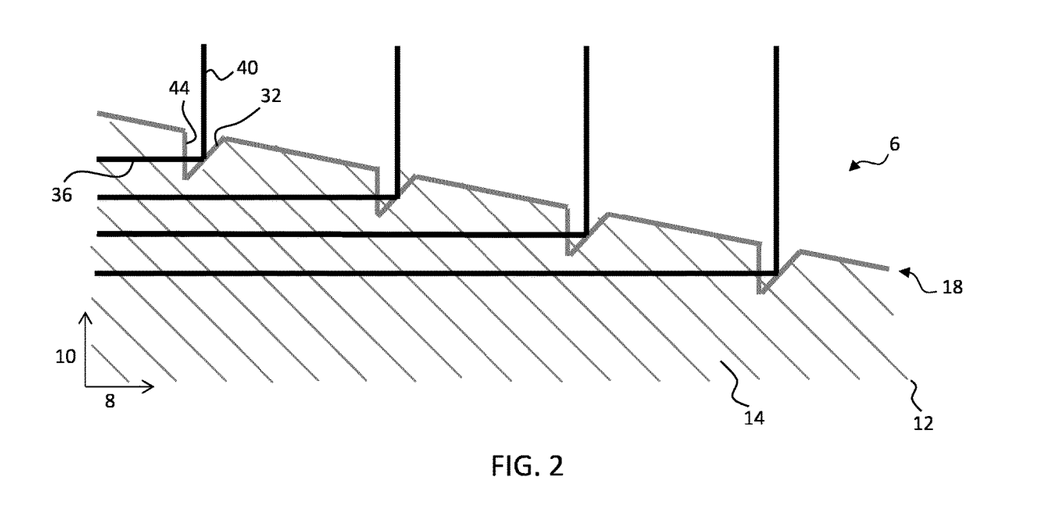
FIG. 2 schematically depicts a second example optical element.

In FIG. 2 is illustrated a second example optical element 6 in accordance with embodiments of the invention. In this embodiment the same optical effect is produced as in the embodiment of FIG. 1, but without the requirement to provide additional optical ring structures 30. Instead, beam deflecting facets 32 are built into the structure of the optical fibre (optical body) 14 itself, as reflective, inclined faces of notches cut into the radial periphery 18. The radius of the element does not decrease stepwise in this case, but rather decreases continuously (excluding the geometry of the notches themselves), and the notches are cut into the periphery at successive axial positions along the element, sufficiently spaced for the change in radius to be greater than or equal to the height of the preceding notch (to avoid overlap). Each notch comprises a first 'vertical' surface 44, through which light is transmitted on incidence from an axial direction, and a second, opposing (inclined) surface 32, disposed at an angle of around 45 degrees to the first surface 44, such that light incident upon it from an axial direction is deflected in a substantially radial direction.

The inclined surface 32 of the notch may be deposited with a reflective coating, for example. A reflective coating could be applied selectively to the oblique surface 32, with vertical surface 44 left transparent, for transmission of axially incident light.

In both of the above described example embodiments, the optical element 6 is combined into or around a transparent optical fibre 14, the fibre facilitating efficient propagation of the beams from the generating source of the light to the deflection facets for redirection radially outwards. However, these embodiments require combination of different materials into a single unit in order to achieve the desired optical effect. This is because the optical fibre—which must be formed of transparent material—must be provided with deflecting facets which are made of reflective material.

This requirement to combine different materials in a single unit is in general undesirable for a variety of reasons, including for example in terms of processing, logistics and cost price. Preferred may be embodiments in which no one unit or module is required to comprise both reflective and transparent elements.

Figure 3:
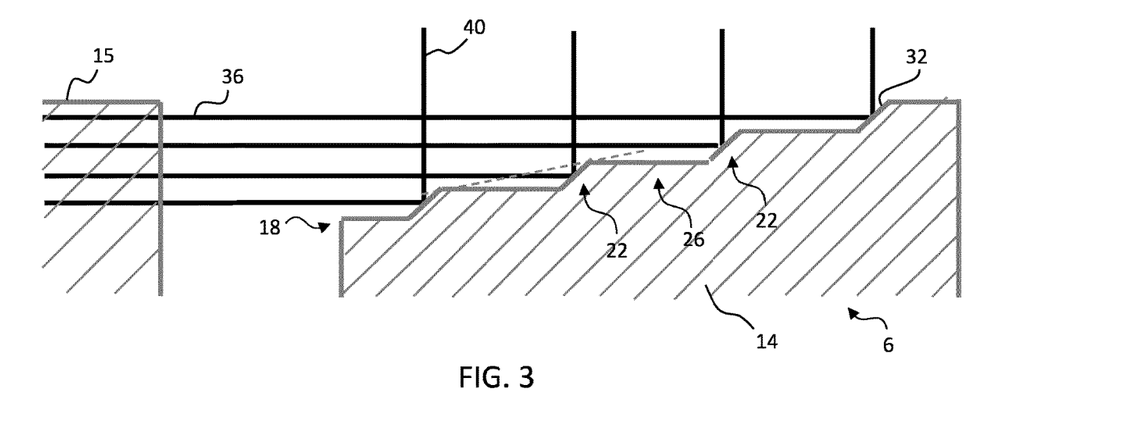
FIG. 3 schematically depicts a third example optical element.

Hence according to third example embodiment, depicted in FIG. 3, there is provided an optical element 6 comprising an optical body consisting of a fully reflective end-piece 14, which may be provided with source light for deflection by means of an optical fibre 15 (separately provided or included as part of the element 6), positioned in axial alignment with, but possibly spatially separated from, the optical body 14 itself.

The optical body 14 comprises a body having a step-wise increasing radius, i.e. increasing stepwise in the direction of the incident light. The radial periphery 18 of the optical body 14 comprises a series of axially spaced, inclined step portions 22, separated by a correspondingly spaced series of axially (or azimuthally) 'flat' portions 26. The outer surfaces of the inclined step portions form reflective deflection facets 32 for deflecting axially incident rays 36 into radial projections 40. As in the example of FIG. 1, the optical body may be axisymmetric, in which case the flat portions 26 effectively define as a series of adjoined cylinders of ever increasing radius, separated from one another by truncated cone sections defined by the inclined step portions 22.

As illustrated in FIG. 3, the optical body 14 must be accurately aligned with the optical fibre core 15, such that light propagated through said core aligns with the deflection facets 32 of the element. According to one or more examples, accurate alignment may be assisted by means of integrating or coupling the end piece 14 to the cladding and/or buffer of the optical fibre 15 itself.

The example of FIG. 3 hence avoids the necessity to combine different materials into a single unit, by providing an entirely reflective optical body 14 which is separate and distinct from any (transparent) optical fibre used for transporting light from its source to the end of the reflective element.

An alternative solution, however, is to exploit total internal reflection effects, using an optical fibre based element, having stepped boundary portions specially shaped and angled so as to generate the desired axially separated radial projections.

Figure 4:
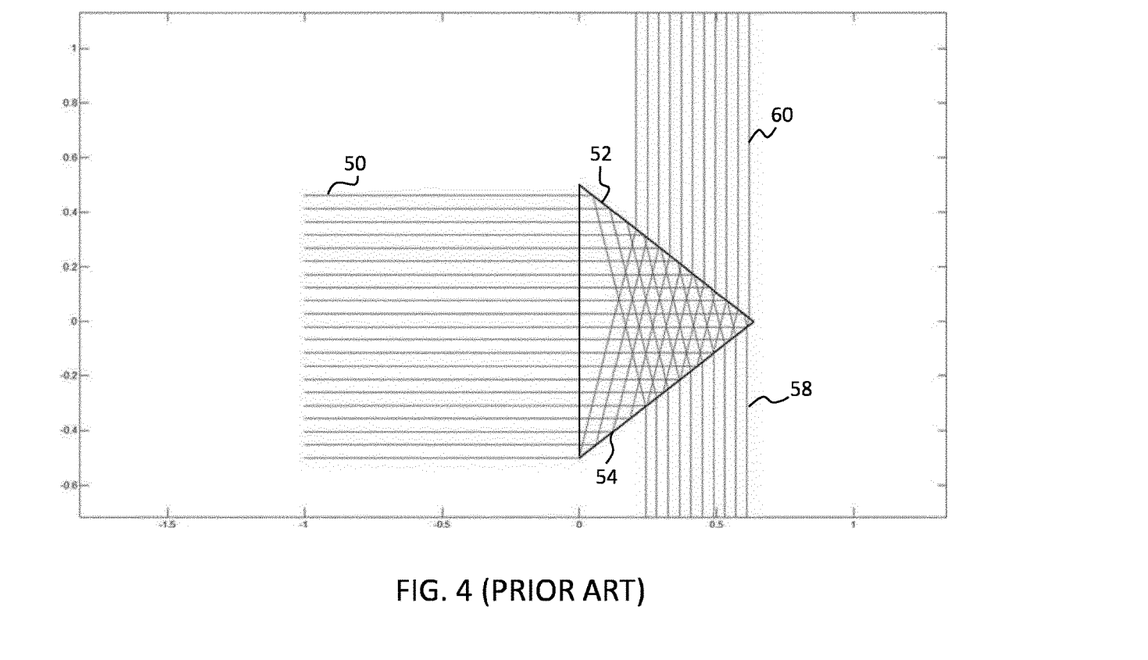
FIG. 4 depicts an example deflecting optical element as known in the art.

In FIG. 4 is depicted a cross-sectional view of an example of a total internal reflector which redirects all horizontal rays 50 into a vertical plane. The reflector comprises a transparent cone, having a boundary which may be notionally divided into an upper 52 and lower 54 boundary portion. Incoming light 50 axially incident at the upper boundary portion 52 is reflected downward through the body of the cone, where it falls incident on the lower boundary portion, and is transmitted out of the cone, bending due to refraction as it does so, to thereby provide an outgoing ray 58 aligned with the vertical plane. Likewise, incoming light 50 axially incident at the lower boundary portion 54 is reflected upwards through the body of the cone and then transmitted out through the upper boundary portion 52, bending into a vertically aligned ray as it does so.

The pitch or tip angle of the cone must be must be specially adapted to the particular refractive index of the cone material, in order to achieve the desired angular deflection. In the particular example of FIG. 4, a cone tip angle of approximately 38 degrees is used for a material with a refractive index of 1.5.

It would be desirable to utilise the underlying principles of this cone in order to provide a total internal reflection based optical element capable of generating discrete, axially spaced radial projections, rather than the axially continuous radial projection produced by the cone.

One means of achieving this is would be to make the cone discontinuous; to separate the cone out into a plurality of vertical 'slices', separated by intermediate cylinder portions having axially parallel outer boundaries. Such an embodiment however, requires very careful dimensional specifications and restrictions in order to avoid stray light escaping through facets which do not have the requisite angle to bend the light into a radial direction.

Figure 5:
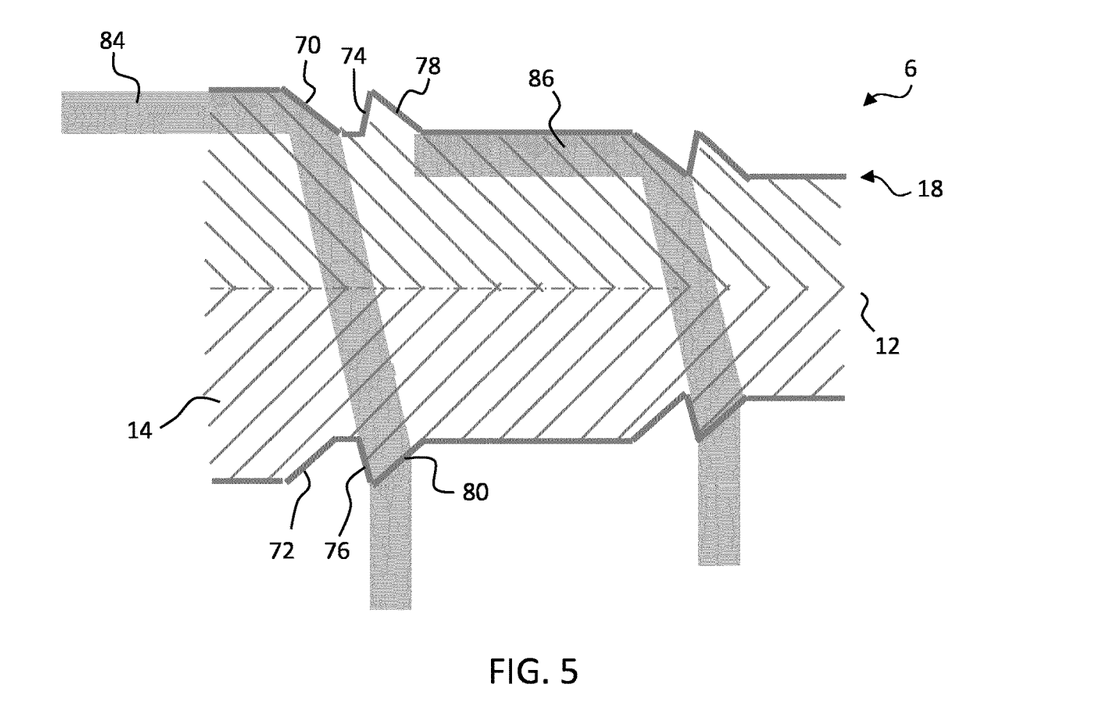
FIG. 5 schematically depicts a fourth example optical element.

In FIG. 5 is shown a cross-section through an example total internal reflection based optical element 6, utilising the principles of the cone shown in FIG. 4. The element comprises an optical body 14 which is axisymmetric about central axial axis 12, and both the top half and the bottom half of the structure are shown. The radial periphery 18 of the structure comprises a series of axially spaced stepped regions, separated by axially parallel sections, each stepped region comprising three successively arranged, alternately inclined surfaces (or facets). The first facet (radially opposite points of which are indicated by 70 and 72 in the figure) acts to deflect axially incident rays radially inwards through the body of the element, toward a section of the third facet (radially opposite points of which are indicated by 78 and 80) on the radially opposite side. The third facet adjoins an alternately inclined, intermediate facet (radially opposite points indicated by 74 and 76), the two together forming an outward protrusion from the structure. The third facet 78, 80 is so axially spaced from the first 70, 72 that light reflected from the first facet exactly coincides with the third facet on the opposite side of the element after propagating across the core of the structure. Furthermore, the third facet is angled so as to transmit all of the light incident upon it from the direction of the first facet on the radially opposite side of the structure.

The first facet furthermore plays a secondary role within the element: namely acting as a 'blocking' facet to prevent axially parallel light being transmitted directly though the transmitting third facet 78, 80. Hence a point of the deflection facet 70 at an upper side of the element both deflects axially incoming light 84 toward a radially opposite point 80 of the third (transmission) facet, but also in so doing acts to block the transmission of axially directed light through a directly radially aligned point 78 of the transmission facet.

For the optical element to function in the desired way, the angular orientations of the three facets, the relative axial positions of the facets, and the relative radial positions of stepped regions must all be controlled to meet certain necessary constraints and relationships. These constraints and relationships will now be discussed in detail, with reference to FIG. 6, which shows an optical diagram corresponding to a section of the embodiment of FIG. 5.

In the description which follows, it is assumed (for purposes of illustration) that the axially directed source light comprises a bundle of radially contiguous light beams. In alternative examples, the source light may simply comprise a single beam, having a continuous beam-front, for example.

Figure 6:
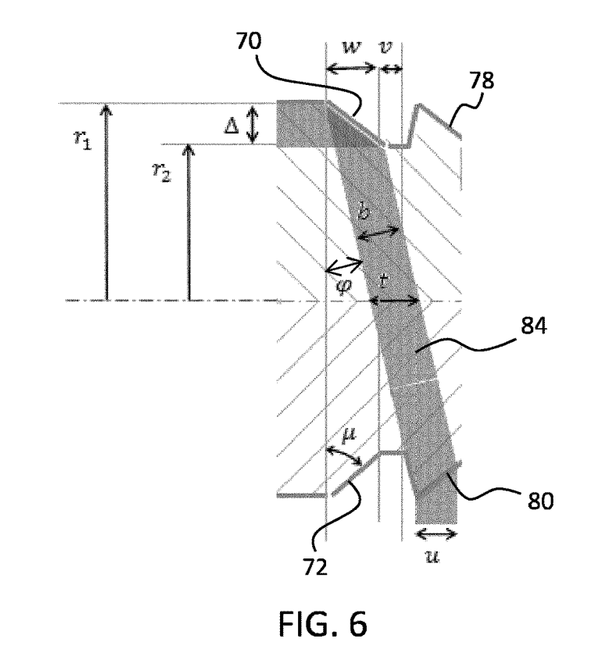
FIG. 6 illustrates an optical diagram corresponding to the fourth example optical element.

The outermost ring 84 of the horizontal bundle is internally reflected by an upper point of the first facet 70 at angle $\mu$ with the vertical, it crosses the transparent material under an angle $\varphi$ with the vertical and exits via a lower point of the third facet 80, also disposed at an angle, $\mu$, and which is positioned at the same radius as the first facet 70 but displaced in the axial direction. The bottom part of the outermost ring 84 is not shown, but it can be verified that this part will reflect at the lower point of the first facet 72 and not on the lower point of the third (transmission) facet 80. A second ring 86 can be deflected in a similar way with the only difference being that the axial displacement of the third (transmission) facet 78, 80 with respect to the first (deflection) facet 70, 72 is less as the (radial) crossing distance at this section of the element is reduced.

For the design of the embodiment of FIGS. 5 and 6, a set of constraining formulas may be derived, with reference to FIG. 6:

$\Delta = r_1 - r_2$ $w = \Delta \tan \mu$ $t = \Delta(\tan \mu - \tan \varphi)$ $v = (r_1 + r_2)\tan \varphi - \Delta \tan \mu = (2r_1 - \Delta)\tan \varphi - \Delta \mu$ $b = t \cos \varphi$ $u = \Delta(\tan \mu - \tan \varphi)\cos \varphi \sin \mu$ (1)

At the first (reflection) surface 70 the angle of incidence equals the angle of reflection. From this we conclude that $$\varphi = 2\mu - \frac{\pi}{2} \qquad (2)$$

The value for $\mu$ can be solved from the refraction law at the lower third (transmission) surface:

$n_t \sin \vartheta_t = n_a \sin \vartheta_a$ (3)

with t, a referring to transparent material and air. The angle of incidence can be easily constructed:

$\vartheta_t = \pi - 3\mu$ (4)

In order to have perpendicular total internal reflection, the angle of refraction should satisfy $$\vartheta_a = \frac{\pi}{2} - \mu \qquad (5)$$

Thus the value for $\mu$ can be solved from $$\frac{\cos \mu}{\sin 3\mu} = \frac{n_t}{n_a} \qquad (6)$$

Note that $\mu$ is also the angle of incidence for all collimated rays on the first facet 70.

For $n_t = 1.5$ and $n_a = 1.0$, we find
$\mu = 51.9°$
The angle of the reflected rays inside the element follows from (2):
$\varphi = 13.8°$
The angle of incidence for the internal deflection facet 70 ($\mu$) is indeed larger than the total internal reflection limit $^{-1}(n_a/n_t)$ in this case, being 41.8 degrees.

The width of the exiting light ring ($\mu$) is a fixed fraction of the incoming ring width ($\Delta$).

It is important to keep a non-zero distance between the first (deflection) facet 70, 72 and third (exit) facet 78, 80; the distance v should not become negative. From this condition we may derive the following constraint for the ring width (i.e. radius reduction) as a function of the initial radius $r_1$:

$$\Delta \leq \frac{2r_1 \tan \varphi}{\tan \mu + \tan \varphi} \qquad (7)$$

For $n_t = 1.5$ and $n_a = 1.0$, we have $\Delta \leq 0.32\ r_1$. It can be checked in FIG. 5 that the first ring 84 deflection still leaves some horizontal margin between first (deflection) facet 70, 72 and the second (exit) facet 78, 80 ($\Delta \approx r_1/4$), but at the second ring 86 deflection there is no margin left (Δ≈r₁/3). In general the constraint (7) gets more restrictive with increasing ring deflection number.

From the point where the ring width can no longer be kept constant the radius reduction can be maximized by first solving $r_{i+1}$ from (7) with $\Delta=r_i-r_{i+1}$, giving the recursive formula:

$$r_{i+1} \geq \frac{\tan\mu - \tan\varphi}{\tan\mu + \tan\varphi} r_i \qquad (8)$$

and next taking the minimum value. For $n_r=1.5$ and $n_a=1.0$, the reduction factor is about ⅔, in other words maximally one third of the radius can be deflected.

The advantage of a total internal reflection embodiment is that no other materials (or coatings) have to be added to the optical core. However, in this case, the core may require protecting by means of a cladding and buffer.

In the case that the fiber core with first 70, 72 and third 78, 80 facet pairs is tightly contained within a transparent cladding, the geometry may require optimization for the refractive index of the cladding material. Typical refractive index values for an optical fiber are $n_{core}=1.62$ and $n_{clad}=1.52$. The total internal reflection limit is in this case $\sin^{-1}(n_{clad}/n_{core})=69.8°$ while the required facet angle satisfying (6) in this case is 51.9 degrees, meaning that this cladding material is not suited for tightly enclosing the core with the facet features.

Figure 7:
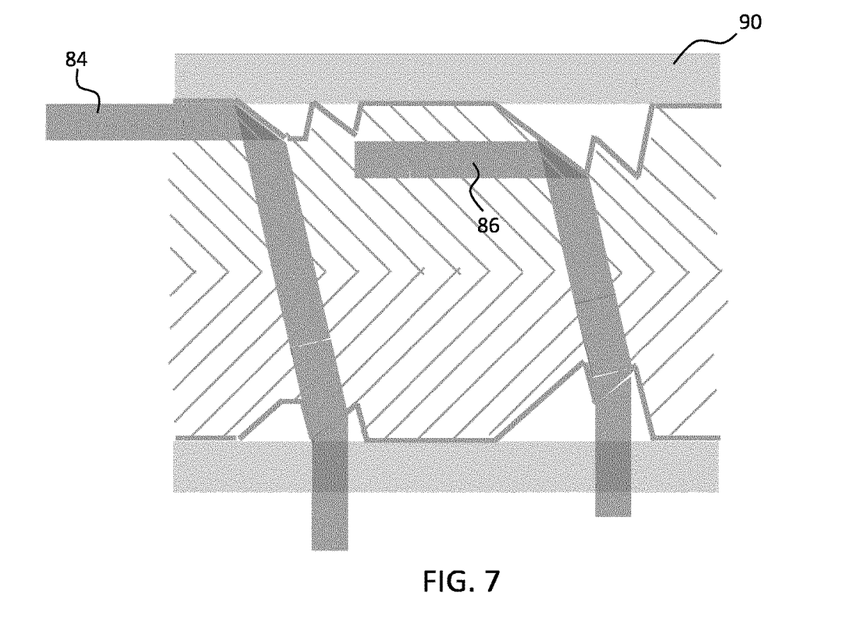
FIG. 7 schematically depicts a fifth example optical element.

The transition towards air (or other surrounding fluid) is assumed in the analysis above, and therefore the fiber core can best be contained in a transparent envelope or capillary leaving air pockets around the facets. In FIG. 7 is depicted an example variation on the design of FIGS. 5 and 6, wherein the outer radius of the element returns to its original (maximum) extension between each of the axially spaced stepped regions. In this way, the element may be directly encapsulated by an outer capillary 90, since, in between the stepped regions, there is a consistent outer radial extension all the way along the structure.

Note that in accordance with any of the above described embodiments, the shape of the element may be adapted so as to follow a helical form. The effect of this is to create radial outward projections which follow a spiral shape.

According to any of the example embodiments, the source beams may be transported by means of an optical fibre (either comprised by the optical element, or provided separately) consisting of core and cladding, and being contained in a protecting buffer (the refractive index of the core and cladding, for example, typically having values of approximately 1.62 and 1.52 respectively.

The collimated source light may, in any example of the invention, be laser light.

The optical structure may in some examples be flexible about its central longitudinal (axial) axis. In this case it is advantageous the facet structures have the flexibility and freedom to reposition with respect to each other by allowing the total longitudinal core (keeping together all facet parts) to bend or flex, in order to follow the longitudinal shape of any curved channel of inspection optimally. In that case the intermediate cylindrical parts need to bend (slightly), but with the radial planes associated with the facet parts maintaining a normal direction aligned with the local longitudinal direction. To deliver the remaining light to the centre of the next facet, a re-collimation structure can be mounted in front of each facet.

According to a further possible example, the optical element may comprise an optical body formed of a hollow cylindrical shell structure, the outer shell layer comprising the radially and axially spaced beam-deflecting facets. In this case, the hollow center of the element may be utilized for carrying electrical or other cables, or for transporting fluid, for example, without affecting the optical functionality of the device. In this case, a collimated cylinder of source light is required to be propagated through the outer shell of the optical element. This might be provided, in examples, by a dedicated arrangement of optical fibers and respective GRIN lenses, arranged in a circular pattern to coincide with the dimensions of the shell of the optical element. Alternatively, there might be provided a single optical element adapted to convert a beam into a circular ring for propagation along the optical element.

Figure 8:
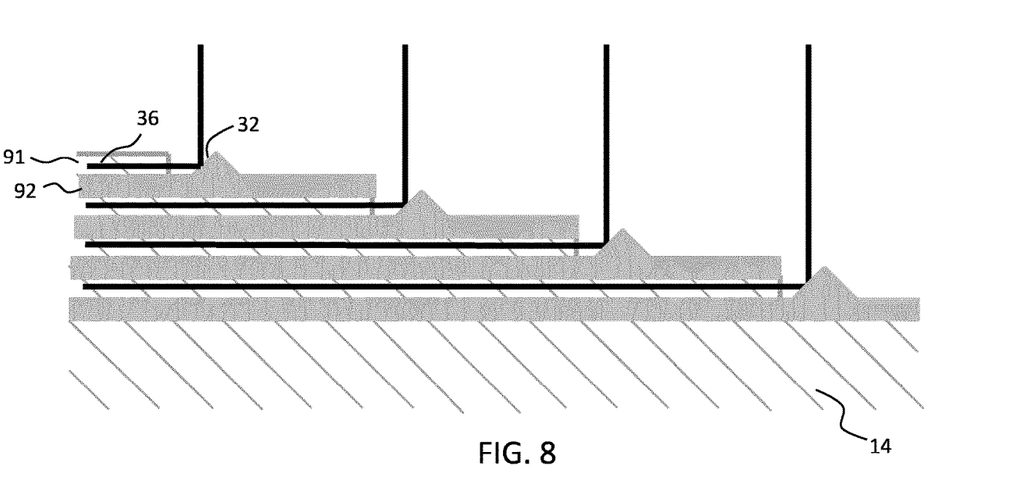
FIG. 8 schematically depicts a sixth example optical element.

In another possibility, illustrated in FIG. 8, the optical element may comprise a 'layered' core, formed of a series of concentrically spaced light transmitting cylindrical layers 91, optically separated from one another by intermediate layers 92, formed of a non-transmitting material. The intermediate layers 92 may in this case comprise the beam deflecting facets 32, arranged to protrude radially from each intermediate layer, and having an inclined surface angled to deflect light from a radially adjacent transmitting layer 91 in an outward radial direction. Each radially deflected ring or 'plane' of light is hence derived from deflection of light passing through a unique one of the transmitting layers.

The embodiment is an adaptation of the embodiment of FIG. 1 in which beam deflecting facets 32 are arranged facing toward stepped portions 22 of the radial periphery of the element 18. One particular advantage of the adaptation is that the separation layers 92 restrict the dispersion of light when the optical element bends. In addition, the deflection features can be easily integrated into the separation layers themselves during manufacturing, contrasting with the FIG. 1 embodiment, which requires separate ringed optical structures 30 to be provided and attached to the core of the element separately.

According to one or more examples, it may be desirable to incorporate features to prevent accidental or unwanted escape of input light from regions of the radial periphery of the optical body of the optical element, not consisting of, or in direct optical communication with, beam-deflecting facets. An example of such an embodiment in shown by way of illustration in FIG. 9. The embodiment consists of the same structure and configuration as the example embodiment of FIG. 2, but includes in addition, a light blocking or arresting layer or diaphragm 99, provided covering the portions of the radial periphery of the optical body 14 lying between each of the beam-deflecting facets 32. The light-arresting cover or diaphragm 99 is adapted to block or otherwise prevent escape of rays from the optical core which are travelling in directions which are not parallel with the axial axis 8, such that they fall incident at one of said intermediate sections of the radial periphery 18.

The addition of such a layer or diaphragm adds greater stability and robustness to the optical functioning of the element, since the element will still function effectively, even in the case that the input beam front is not propagated along the element exactly in alignment with the axial axis of the optical body. This means that the tolerances for the input beam angle may be weakened, rendering the optical element easier and simpler to use and also potentially expanding the possible applications of the optical element.

Figure 9:
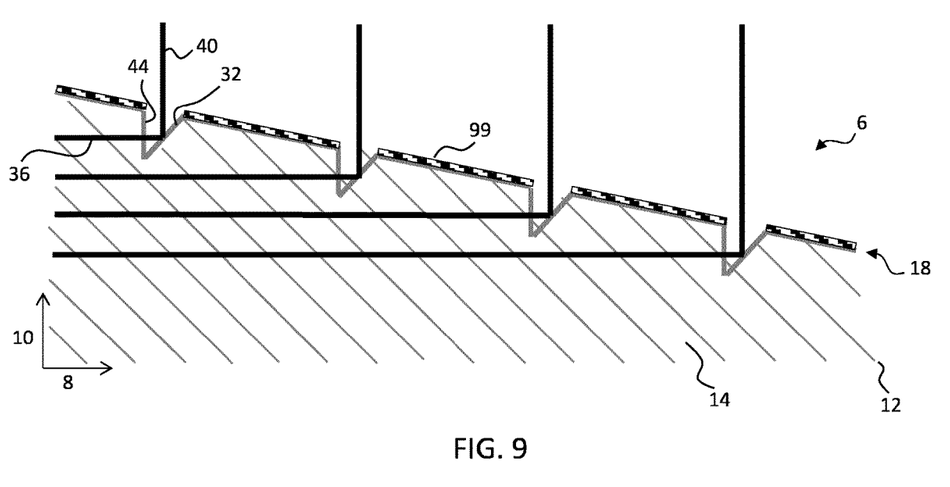
FIG. 9 schematically depicts a seventh example optical element.

According to one or more examples, the light arresting layer, diaphragm or cover 99 may be configured to fully or partially absorb light incident at least at an internal surface of the radial boundary 18. In other examples, the layer or diaphragm 99 may be adapted to fully or partially reflect light incident at an internal surface of the radial boundary 18. Any other physical means of similarly preventing the escape of light may also be used.

In examples, the cover or layer 99 may comprise a metal reflecting layer. In further examples, the layer or envelope 99 may consist of any non-transparent material layer, or layer otherwise adapted to prevent the transmission of light.

According to one or more examples, the cover or envelope 99 may be comprised of, or may be equivalently replaced by one or more destructive interference layers.

The diaphragm or cover 99 may effectively form a covering shell, having slits or spaces in alignment with the beam-deflecting facets.

The light-arresting layer 99 may in examples be formed by depositing, coating or otherwise applying to the outer periphery of the optical body of the optical element a layer of a suitably light-inhibiting material, for example a reflective metal layer or coating. In the case of a metal coating, this might be performed, by firm bending or otherwise shaping a metal layer in correspondence with the contours, profile or shape of the outer periphery, and then applying or depositing the shaped layer to the optical element.

Figure 10:
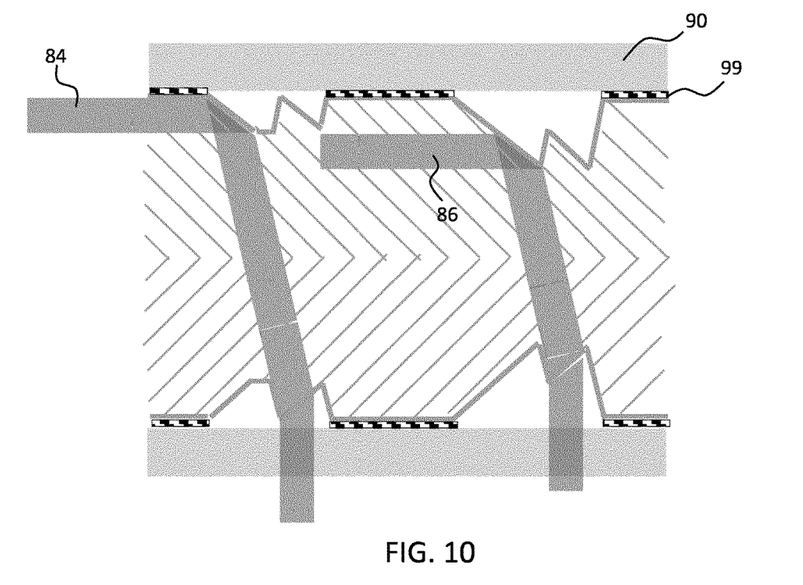
FIG. 10 schematically depicts and eighth example optical element.

By way of further example, FIG. 10 shows an additional example of an embodiment comprising a light-blocking or arresting outer layer 99. Here, the embodiment of FIG. 7 is shown having an appropriate cover or layer 99 provided to intermediate regions of the radial periphery.

In alternative examples, the light-blocking covering layer 99 may be applied not only to intermediate portions of the radial periphery (as shown in the examples of FIGS. 9 and 10), but also to the surfaces of the light-blocking facets themselves. This may simplify fabrication of such an embodiment, since formation of the reflective surfaces of the deflecting facets may be combined into the same process as that of forming the light-blocking envelope or layer 99.

The invention has numerous potential applications. As discussed in preceding sections, one particularly advantageous application is in the field of endoscopy, wherein it is desirable, for optical inspection of a patient's airway, to be able to generate multiple ringed patterns of light, at spaced points along the airway, without the need to provide separate lasers to generate each one. Embodiments of the present invention allow such a plural pattern to be generated, with just a single laser (or other light) source, and single (for example GRIN) collimating lens. This significantly reduces both the bulk and complication of the catheter into which said elements are incorporated, and the cost of manufacturing such a catheter.

Figure 11:
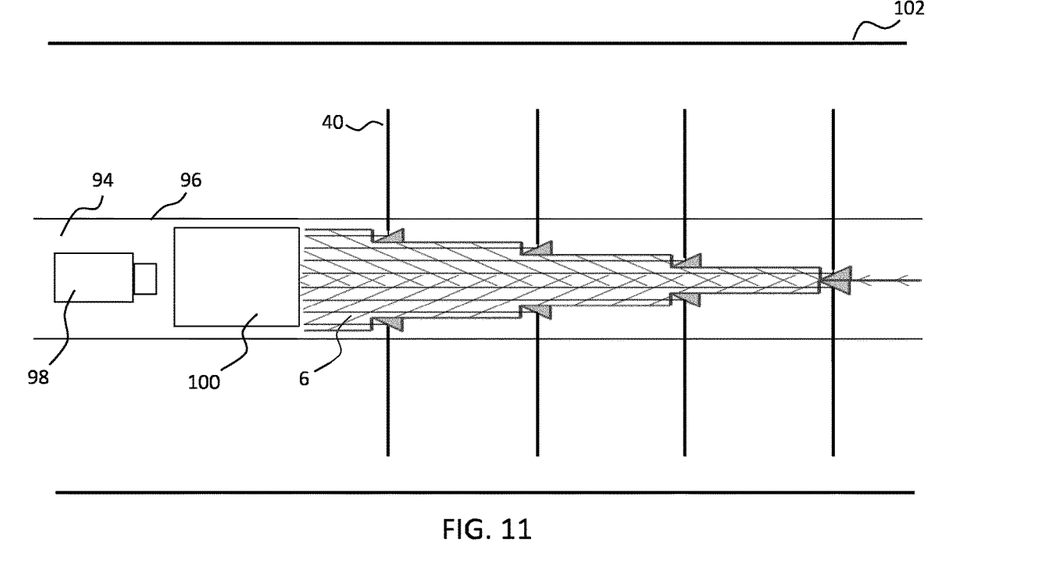
FIG. 11 schematically depicts an example catheter incorporating an embodiment of the optical element.

In FIG. 11 is schematically depicted an illustrative example of a catheter 94 incorporating an optical element as described in embodiments above. The catheter 94, encapsulated within a transparent capillary 96, comprises a laser 98, arranged to propagate generated laser light in the direction of an axially displaced gradient index (GRIN) lens 100. The GRIN lens is optically coupled with the optical element 6. For the particular example of FIG. 11, the optical element of FIG. 1 is depicted. The catheter 96 is shown disposed within a patient airway 102. Source light propagated through the optical element via the GRIN lens 100 is deflected at axially spaced points along the catheter, into a series of radial projections 40, which form ring patterns projected radially outward from the catheter toward the walls of the patient airway 102.

Figure 12:
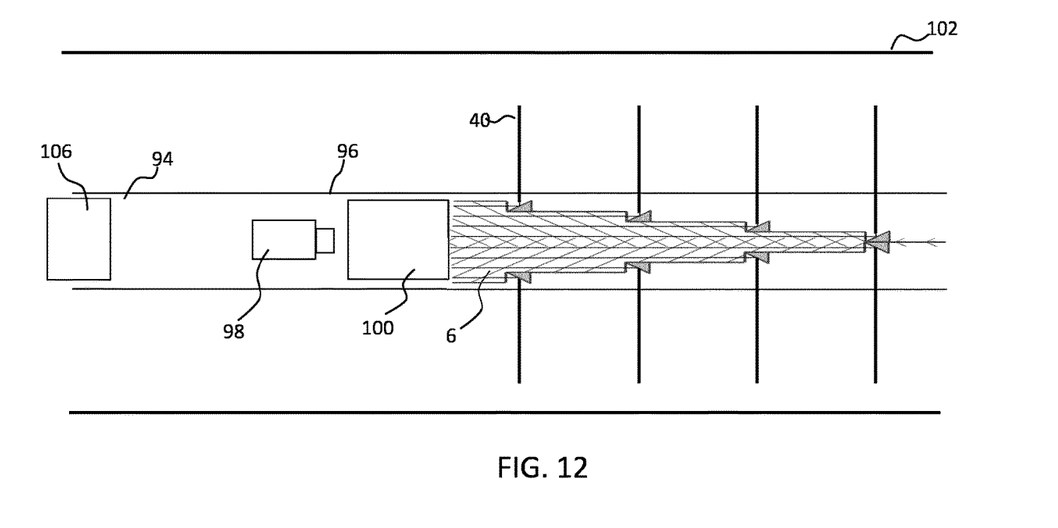
FIG. 12 schematically depicts an example configuration of an imaging system comprising an optical element.

In FIG. 12 is illustrated an example arrangement of an imaging system in accordance with an embodiment of the invention, comprising an optical element and a camera element for capturing light reflected from internal walls of an internal cavity 102. In the example shown, the imaging system is depicted as incorporated within the example catheter arrangement 94 depicted in FIG. 11 (and described above). The camera element of the example of FIG. 12 is adapted to generate a field of view which extends across two (possibly disjointed) angular regions as shown, with the first region angled and shaped to capture reflections generated from each of an upper set of projections, and the second region angled and shaped so as to capture reflections from each of a lower set of projections. The upper and lower set of projections in practice may comprise first and second (upper and lower) radial regions of a set of axially separated annular projections 40. Furthermore, in examples, the camera element may be adapted to capture light across a a circular or annular or field of view, of which the depicted two fields of view in FIG. 12 constitute merely a planar cross-section.

According to further examples, the imaging system may comprise a plurality of camera elements, each adapted to capture light across a substantially different field of view. These fields of view may however overlap to some extent. The plurality of camera elements may be positioned at substantially the same axial position, or may be positioned at differing axial points along the the length of the optical element or along the length of a catheter comprising the optical element for instance.

The advantage of generating multiple axially spaced rings of light is that multiple contour images may be captured by a catheter camera 106 or sensor simultaneously. In addition, the parallel light planes may also be uniquely tagged in their transit through the transparent cylindrical window (capillary) 96 by means of an additional circumferential bar or dot code on or in the window. This tagging may allow the unique identification of multiple contours (rings), or radial sections of multiple rings, in a single camera image.

The optical element may be incorporated directly within an endoscope, or may be built into a separate illumination device that can be used in combination with any existing endoscope. The illumination fibre is very thin and provides distributed lighting. Hence, endoscopes may be used, in combination with embodiments of the invention, which do not have illumination elements built into them. As a result, endoscopes may be made having much smaller diameter.

The endoscope operator will experience a sense of depth when the airway is lit by a series of rings at regular distances. In state of the art endoscopes, having a tip light, it often occurs that the sides of the patient airway are brightly lit, while the centre only shows a black hole. Partial obstructions will be more easily identifiable, since they will block the line of sight between more distance rings (behind the obstruction) and the camera (in front of the obstruction).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measured cannot be used to advantage. Any reference signs in the claims should not be construed as limiting the scope.

The invention claimed is:

1. An imaging system for imaging an internal cavity, comprising:
   an optical element, comprising:
      a single optical body having axial extension and radial extension, for receiving an input beam-front which propagates in the axial direction, and deflecting said input beam front into a series of axially spaced annular projections of light, and
      a plurality of beam-deflecting facets, axially and radially separated with respect to one another, with non-beam-deflecting spaces in between, wherein the beam-deflecting facets are arranged along the optical body and configured to directly intercept the input beam-front and deflect different annular portions of the input beam-front outwards from the optical body, in a radial direction, to thereby generate from the optical element a series of axially separated annular projections of light; and
   an image collection means for collecting light reflected from one or more surfaces of the internal cavity.

2. An imaging system as claimed in claim 1, wherein the radial extension of the optical body varies along the axial direction, and wherein the beam-deflecting facets are arranged at axially successive points along a radial periphery of the optical body.

3. An imaging system as claimed in claim 2, wherein the radial extension of the optical body progressively decreases or progressively increases along the axial direction.

4. An imaging system as claimed in claim 2, wherein the overall envelope of radial extension of the optical body, excluding any protrusions or depressions formed by the beam-deflecting facets, varies continuously along the axial direction.

5. An imaging system as claimed in claim 2, wherein the radial extension of the optical body varies stepwise along the axial direction, such that the radial periphery of the optical body comprises a series of axially spaced stepped portions.

6. An imaging system as claimed in claim 5, wherein the beam-deflecting facets are comprised by reflecting elements, each having a reflective surface arranged facing one of said stepped portions, and angled so as to reflect axially incident light outward from the element in a radial direction.

7. An imaging system as claimed in claim 2, wherein the beam-deflecting facets partly delimit the radial periphery of the optical body.

8. An imaging system as claimed in claim 7, wherein the beam-deflecting facets form stepped portions in the radial periphery, and wherein each beam-deflecting facet is arranged to deflect light outwards from the element via a corresponding transmission facet positioned at a radially opposite point on the radial periphery, said point positioned along an optical path through the optical body from the deflecting facet.

9. An imaging system as claimed in claim 8, wherein each transmission facet partly delimits the radial periphery of the optical body, and wherein the deflecting facets reflect light by total internal reflection.

10. An imaging system as claimed in claim 9, wherein for each transmission facet, there is provided, at a radially parallel and axially adjacent point along the radial periphery, a corresponding blocking facet, arranged to reflect rays incident from an axial direction, to prevent said rays being transmitted through the corresponding transmission facet.

11. An imaging system as claimed in claim 10, wherein the radial extension of the optical body decreases along the axial direction, and wherein, for at least an axial portion of the optical body, the radial extensions $r_i$ at axially successive deflecting facets conform to $$r_{i+1} \geq \frac{\tan\mu - \tan\varphi}{\tan\mu + \tan\varphi} r_i$$

where $\mu$=angle of the deflecting facet, and $\varphi$=propagation angle of the beam(s), with respect to a radial direction, after reflection by the deflecting facet.

12. An imaging system as claimed in claim 1, wherein the optical body comprises an optical fibre.

13. A catheter or endoscope comprising:
   a beam generating means; and
   an imaging system as claimed in claim 1, the optical element being in optical communication with said beam generating means and arranged so as to deflect light from the beam generating means radially outward from the catheter or endoscope.

14. A method of imaging an internal cavity including deflecting axially propagated light to form a series of axially spaced, annular projections, the method comprising:
   propagating an input beam-front in an axial direction along an optical body comprised by an optical element, the optical element being positioned within the internal cavity, and said optical body having axial extension and radial extension, wherein the optical element further comprises a plurality of beam-deflecting facets, the beam-deflecting facets being axially and radially separated with respect to one another, with non beam-deflecting spaces in between, and arranged so as to directly intercept the input beam-front and deflect different annular portions of the input beam-front outwards from the optical element, in a radial direction, to thereby generate from the optical element a series of axially separated annular projections of light; and
   collecting light reflected by one or more surfaces of the internal cavity by means of an image collection means, to thereby enable imaging of the internal cavity.

15. A method as claimed in claim 14, wherein the light beams are laser beams.

16. An imaging system for imaging an internal cavity, comprising:
   an optical element, comprising
      a single optical body having axial extension and radial extension, for receiving an input beam-front which propagates in the axial direction, and deflecting said input beam front into a series of axially spaced annular projections of light, and
      a plurality of beam-deflecting facets, axially and radially separated with respect to one another, with non-beam-deflecting spaces in between, wherein the beam-deflecting facets are arranged along the optical body and configured to intercept and deflect different annular portions of the input beam-front outwards from the optical body, in a radial direction, to thereby generate from the optical element a series of axially separated annular projections of light; and
   an image collection means for collecting light reflected from one or more surfaces of the internal cavity,
   wherein the radial extension of the optical body varies along the axial direction,
   wherein the beam-deflecting facets are arranged at axially successive points along a radial periphery of the optical body, wherein the beam-deflecting facets partly delimit the radial periphery of the optical body, wherein the beam-deflecting facets form stepped portions in the radial periphery, wherein each beam-deflecting facet is arranged to deflect light outwards from the element via a corresponding transmission facet positioned at a radially opposite point on the radial periphery, said point positioned along an optical path through the optical body from the beam-deflecting facet, wherein each transmission facet partly delimits the radial periphery of the optical body, wherein the deflecting facets reflect light by total internal reflection, and wherein for each transmission facet, there is provided, at a radially parallel and axially adjacent point along the radial periphery, a corresponding blocking facet, arranged to reflect rays incident from an axial direction, to prevent said rays being transmitted through the corresponding transmission facet.

17. An imaging system as claimed in claim 16, wherein the radial extension of the optical body decreases along the axial direction, and wherein, for at least an axial portion of the optical body, the radial extensions $r_i$ at axially successive deflecting facets conform to $$r_{i+1} \geq \frac{\tan\mu - \tan\varphi}{\tan\mu + \tan\varphi} r_i$$

where $\mu$=angle of the deflecting facet, and $\varphi$=propagation angle of the beam(s), with respect to a radial direction, after reflection by the deflecting facet.

18. An imaging system as claimed in claim 1, wherein the optical body is arranged to receive the input beam-front in the optical body before the input beam-front reaches the plurality of beam-deflecting facets.

* * * * *